(12) United States Patent
Kubokawa et al.

(10) Patent No.: US 7,804,461 B2
(45) Date of Patent: Sep. 28, 2010

(54) ANTENNA COVER AND ANTENNA APPARATUS

(75) Inventors: Hiroaki Kubokawa, Sagamihara (JP); Kazutaka Nakatsuchi, Hino (JP)

(73) Assignee: Olympus Corporation, Tokyo (JP)

( * ) Notice: Subject to any disclaimer, the term of this patent is extended or adjusted under 35 U.S.C. 154(b) by 309 days.

(21) Appl. No.: 12/146,342

(22) Filed: Jun. 25, 2008

(65) Prior Publication Data

US 2008/0291112 A1 Nov. 27, 2008

Related U.S. Application Data

(62) Division of application No. 11/629,761, filed as application No. PCT/JP2005/010972 on Jun. 15, 2005, now Pat. No. 7,456,801.

(30) Foreign Application Priority Data

| Jun. 16, 2004 | (JP) | ............................. 2004-178562 |
| Jun. 23, 2004 | (JP) | ............................. 2004-185554 |
| Jun. 23, 2004 | (JP) | ............................. 2004-185555 |

(51) Int. Cl.
*H01Q 1/42* (2006.01)

(52) U.S. Cl. ..................................... 343/872

(58) Field of Classification Search ................ 343/872; 383/37, 38, 93
See application file for complete search history.

(56) References Cited

U.S. PATENT DOCUMENTS

| 2,991,001 | A | * | 7/1961 | Hughes | .................... 383/210.1 |
| 3,889,871 | A | * | 6/1975 | White | ......................... 383/203 |
| 4,786,190 | A | * | 11/1988 | Van Erden et al. | .......... 383/203 |
| 6,012,844 | A |   | 1/2000 | Huseman et al. | |
| 6,575,627 | B2 | * | 6/2003 | Huseman et al. | .............. 383/38 |

| 2002/0179721 | A1 | 12/2002 | Elbaz et al. |
| 2004/0231771 | A1 | 11/2004 | Shiue |

(Continued)

FOREIGN PATENT DOCUMENTS

CN 2342475 Y 10/1999

(Continued)

OTHER PUBLICATIONS

Japanese Office Action dated Oct. 2, 2007 with English translation.

(Continued)

*Primary Examiner*—Hoang V Nguyen
(74) *Attorney, Agent, or Firm*—Scully, Scott, Murphy & Presser, P.C.

(57) ABSTRACT

After a receiving antenna (A1) is inserted from a slot (B16) into a housing portion (B14) formed between cover members (B11, B12), the slot (B16) is pasted so as to secure the receiving antenna (A1). The receiving antenna (A1) is thus housed. Further, a tab (B17) which extends from one side of a pasted edge portion, holes (B20, B21) that penetrate opposing surfaces of the cover members (B11, B12), and perforated lines (B22, B23) running from the slot (B16) to the holes (B20, B21), respectively, are provided. Therefore, the receiving antenna (A1) can be easily attached to the antenna cover (B1) and to an outer surface of a subject (1), and the receiving antenna (A1) can be easily removed from the antenna cover (B1) and from the outer surface of the subject (1).

5 Claims, 10 Drawing Sheets

U.S. PATENT DOCUMENTS

2006/0196792 A1    9/2006    Barth et al.

FOREIGN PATENT DOCUMENTS

| | | |
|---|---|---|
| CN | 1279797 A | 1/2001 |
| JP | S58-164305 | 11/1983 |
| JP | H04-137802 | 5/1992 |
| JP | 9-098006 | 4/1997 |
| JP | H09-098006 | 4/1997 |
| JP | H09-117439 | 5/1997 |
| JP | H10-211080 | 8/1998 |
| JP | 10-233612 | 9/1998 |
| JP | 11-078323 | 3/1999 |
| JP | 11-214910 | 8/1999 |
| JP | 2000-025837 | 1/2000 |
| JP | 2002-274562 | 9/2002 |
| JP | 2003-019111 | 1/2003 |
| JP | 2003-044810 | 2/2003 |
| JP | 2003-170986 | 6/2003 |
| JP | 2003-521972 A | 7/2003 |
| WO | WO 97/18137 | 5/1997 |
| WO | WO 98/50280 | 11/1998 |
| WO | 01/28416 A1 | 4/2001 |
| WO | WO 2004/039233 A2 | 5/2004 |

OTHER PUBLICATIONS

Notice of Allowance dated Oct. 27, 2009 received from the Japanese Patent Office.
Japanese Office Action dated Oct. 27, 2009 with English translation.
Notice of Allowance dated Oct. 27, 2009 received from the Japanese Patent Office.
Chinese Official Action dated Mar. 9, 2010.

* cited by examiner

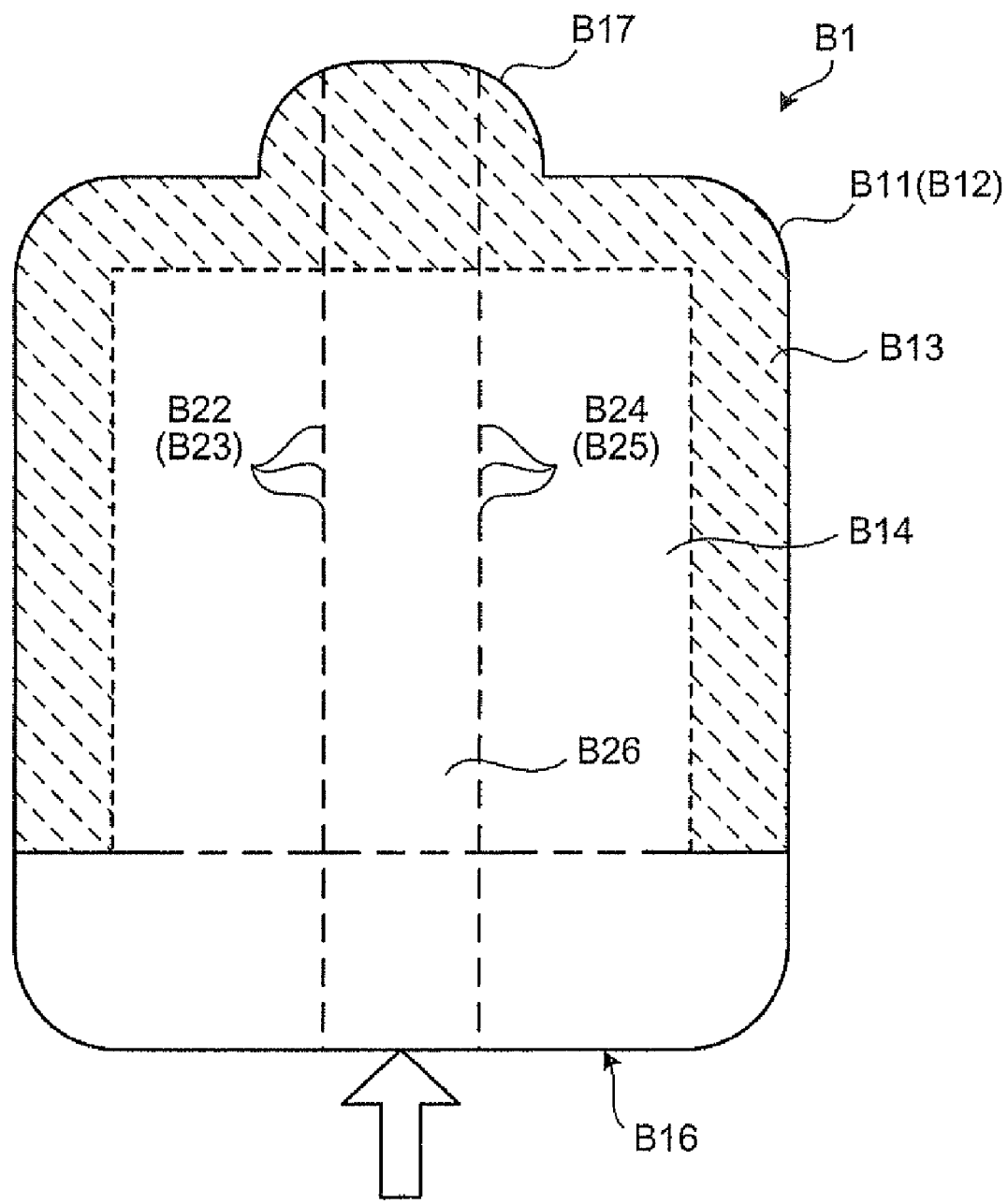

ANTENNA COVER AND ANTENNA APPARATUS

CROSS REFERENCE TO RELATED APPLICATION

This application is a divisional application of U.S. application Ser. No. 11/629,761 filed on Dec. 15, 2006, now U.S. Pat. No. 7,456,801, which claims the benefit of priority from Japanese Patent Application Nos. 2004-178562 filed on Jun. 16, 2004; 2004-185554 filed on Jun. 23, 2004; 2004-185555 filed on Jun. 23, 2004; and PCT Application No. PCT/JP2005/010972 filed on Jun. 15, 2005, of each of which are incorporated herein by their reference.

TECHNICAL FIELD

The present invention relates to an antenna cover and an antenna apparatus that house an antenna element inside, and more particularly to an antenna cover and an antenna apparatus that can be pasted on to a surface of a subject.

BACKGROUND ART

In recent years, a capsule endoscope appears in the field of endoscope. The capsule endoscope is equipped with an imaging function and a radio communication function. The capsule endoscope is swallowed from a mouth of a subject for an observation (examination). After being swallowed, the capsule endoscope moves through inside internal organs (body cavities), such as a stomach and a small intestine, following a peristaltic motion inside the subject, and sequentially picks up images inside using the imaging function until being naturally discharged from a living body of the subject (human body), i.e., during an observation period.

While moving inside the internal organs, i.e., during the observation period, the capsule endoscope sequentially transmits image data obtained through imaging inside the body cavities to an outside of the subject using the radio communication function. The transmitted image data is stored in a memory provided inside a receiving device outside. After swallowing the capsule endoscope, the subject carries the receiving device which has radio communication function and memory function until the capsule endoscope is discharged, whereby the subject can move freely without inconveniences even during the observation period. After the observation, a doctor or a nurse can retrieve the image data stored in the memory of the receiving device and watch images inside the body cavities on a display device such as a monitor to make diagnosis.

Generally, the receiving device includes plural antenna elements for receiving image signals transmitted from the capsule endoscope. The antenna elements are arranged in a dispersed manner outside the subject. The receiving device selectively switches to one antenna element, which receives image signals with less reception errors, and uses the selected antenna element for reception. For example, a receiver described in Patent Document 1 has plural antenna elements including adhesive applied thereto. The plural antenna elements adhere to the subject at predetermined positions and thereby arranged outside the subject. The receiver switches from one antenna element to another for reception, and locates a position of the capsule endoscope which is a sender of the image signals and placed inside the subject based on intensities of electric fields received by the respective antenna elements.

Patent Document 1: Japanese Patent Application Laid-Open No. 2003-19111

DISCLOSURE OF INVENTION

Problem to be Solved by the Invention

When an operator directly attaches the plural antenna elements on the surface of the subject at various positions, however, operations to attach the plural antenna elements before an examination and to remove the same after the examination become cumbersome. Such a procedure is troublesome and takes time. Accordingly, the examination takes a longer time.

In view of the foregoing, an object of the present invention is to provide an antenna cover and an antenna apparatus that house an antenna element in the antenna cover and that can facilitate an operation to attach the antenna element to the subject or to the antenna cover before an examination and an operation to remove the antenna element from the subject or from the antenna cover after the examination.

Means for Solving Problem

An antenna cover according to one aspect of the present invention includes a cover member which forms a housing portion inside, the housing portion being able to accommodate at least a portion of an antenna element; a slot which is formed in the cover member, and through which the antenna element can be inserted to the housing portion; an adhesive portion which is provided on the slot, which guides a cable extending from the antenna element and which has adhesiveness to paste and close the slot when the antenna element is accommodated in the housing portion.

The antenna cover may further include a breakable portion which is formed substantially colinearly with a direction of extension of the cable so as to allow breakage of the cover member.

In the antenna cover, the breakable portion may have a continuous thin portion which is formed in the cover member so as to extend from the slot in an opposite direction to the direction of extension of the cable, and the breakable portion is formed so as to be breakable when acted upon by an external force which is applied in a direction substantially perpendicular to the direction of extension.

In the antenna cover, the breakable portion may have a continuous perforation which is formed in the cover member so as to extend from the slot in an opposite direction to the direction of extension of the cable, and the breakable portion is formed so as to be breakable when acted upon by an external force which is applied in a direction substantially perpendicular to the direction of extension.

In the antenna cover, the breakable portion may have a deformable portion which is formed in the cover member so as to extend from the slot in an opposite direction to the direction of extension of the cable, and the breakable portion is formed so as to be breakable when acted upon by an external force which is applied in a direction substantially perpendicular to the direction of extension.

In the antenna cover, the breakable portion may have an overlapping portion which is formed in the cover member so as to extend from the slot in an opposite direction to the direction of extension of the cable, and the breakable portion is formed so as to be breakable when acted upon by an external force which is applied in a direction substantially perpendicular to the direction of extension.

An antenna cover according to another aspect of the present invention includes a cover member which forms a housing portion inside, the housing portion being able to accommodate at least a portion of an antenna element; a slot which is formed in the cover member, and through which the antenna element can be inserted into the housing portion; an adhesive portion which is formed on a predetermined surface of the cover member and which has adhesiveness to allow the cover member to adhere onto a subject; and a non-adhesive portion which is formed on the same predetermined surface of the cover member as the predetermined surface on which the adhesive portion is formed, and which has non-adhesiveness.

In the antenna cover, the antenna cover may further include an extending portion which extends from an edge of the cover member, and the non-adhesive portion is provided on the extending portion at a side of the predetermined surface on which the adhesive portion is formed.

In the antenna cover, the cover member may be formed with sheets of materials such as paper, non-woven fabric, and cellophane pasted with each other.

An antenna cover according to still another aspect of the present invention includes a bag-like cover member which forms a housing portion inside, the housing portion being able to accommodate at least a portion of the antenna element; and a window portion which is formed in the cover member, the window portion being formed in each of opposite surfaces of the bag-like cover member.

In the antenna cover, the cover member may form the housing portion inside, the housing portion is able to accommodate at least a portion of the antenna element, and at least one portion of the cover member is formed of a transparent member, the antenna cover further comprising, a slot which is formed in the cover member and through which the antenna element can be inserted into the housing portion.

In the antenna cover, the cover member may include plural sheets of material such as paper, non-woven fabric, and cellophane, and is formed into a bag-like shape.

An antenna according to still another aspect of the present invention includes at least one antenna element; and an antenna cover which can house at least a portion of the antenna element. The antenna cover includes a cover member which forms a housing portion inside, the housing portion being able to accommodate at least a portion of the antenna element, a slot which is formed in the cover member and through which the antenna element can be inserted into the housing portion, and an adhesive portion which is provided on the slot, which guides a cable extending from the antenna element, and which has adhesiveness to paste and close the slot when the antenna element is accommodated in the housing portion.

In the antenna apparatus, the antenna cover may further include a breakable portion which is formed substantially colinearly with a direction of extension of the cable so as to allow breakage of the cover member.

An antenna apparatus according to still another aspect of the present invention includes at least one antenna element; and an antenna cover which can house at least a portion of the antenna element. The antenna cover includes a cover member which forms a housing portion inside, the housing portion being able to accommodate at least a portion of an antenna element; a slot which is formed in the cover member, and through which the antenna element can be inserted into the housing portion; an adhesive portion which is formed on a predetermined surface of the cover member and which has adhesiveness to paste the cover member onto a subject; and a non-adhesive portion which is formed on a same predetermined surface of the cover member as the predetermined surface on which the adhesive portion is formed, and which has non-adhesiveness.

In the antenna apparatus, the antenna cover may further include an extending portion which extends from an edge of the cover member, and the non-adhesive portion is provided on the extending portion at a side of the predetermined surface on which the adhesive portion is formed.

In the antenna apparatus, the cover member may be formed with sheets of materials such as paper, non-woven fabric, and cellophane pasted with each other.

An antenna apparatus according to still another aspect of the present invention includes at least one antenna element; and an antenna cover which can house at least a portion of the antenna element, the antenna cover including, a cover member which forms a housing portion inside, the housing portion being able to accommodate at least a portion of the antenna element; a slot which is formed in the cover member and through which the antenna element can be inserted into the housing portion; and a window portion which is formed in the cover member, the window portion being formed in each of opposite surfaces of the cover member.

In the antenna apparatus, the antenna element may include a first transparent member which is arranged at a portion facing at least the window portion when the antenna element is accommodated in the housing portion.

In the antenna apparatus, at least a portion of the cover member may be formed with a second transparent member.

In the antenna apparatus, the cover member may include plural sheets of material such as paper, non-woven fabric, and cellophane pasted with each other.

EFFECT OF THE INVENTION

The antenna cover and the antenna apparatus according to the present invention include the cover member which can house at least a portion of the antenna element, whereby the operation to attach the antenna element to the antenna cover or to the subject before the examination and the operation to remove the antenna element from the antenna cover or from the subject after the examination can be readily performed.

Further, the antenna cover and the antenna apparatus according to the present invention include the antenna cover which can house the antenna element inside the housing portion formed in the cover member by receiving the antenna element inserted from the slot. In addition, the antenna cover and the antenna apparatus include the adhesive portion which is provided on the slot, which guides the cable extending from the antenna element, and which has adhesiveness to close the slot by adhesion when the antenna element is housed inside the housing portion. Therefore, the operation to attach the antenna element to the antenna cover or to the subject before the examination and the operation to remove the antenna element from the antenna cover or from the subject after the examination can be readily performed.

Still further, the antenna cover and the antenna apparatus according to the present invention include the antenna cover which houses at least a portion of the antenna element inside the housing portion formed in the cover member by receiving the antenna element inserted from the slot. In addition, the antenna cover and the antenna apparatus include the adhesive portion which is formed on the predetermined surface of the cover member and allows for the antenna cover to be pasted onto the predetermined position on the subject. Therefore, the operation to attach the antenna element to the antenna cover or to the subject before the examination and the operation to remove the antenna element from the antenna cover or from the subject after the examination can be readily performed.

Still further, the antenna cover and the antenna apparatus according to the present invention houses the antenna element inside the antenna cover by receiving and securing the antenna element inserted from the slot inside the housing portion formed in the cover member. In addition, the opening is formed so as to penetrate each of the opposing surfaces of the cover members that form the housing portion. Therefore, the operation to attach the antenna element to the antenna cover or to the subject before the examination and the operation to remove the antenna element from the antenna cover or from the subject after the examination can be readily performed.

BRIEF DESCRIPTION OF DRAWINGS

FIG. 11 is a schematic diagram illustrating another exemplary structure of the antenna cover according to the third embodiment.

EXPLANATIONS OF LETTERS OR NUMERALS

Figure 1:
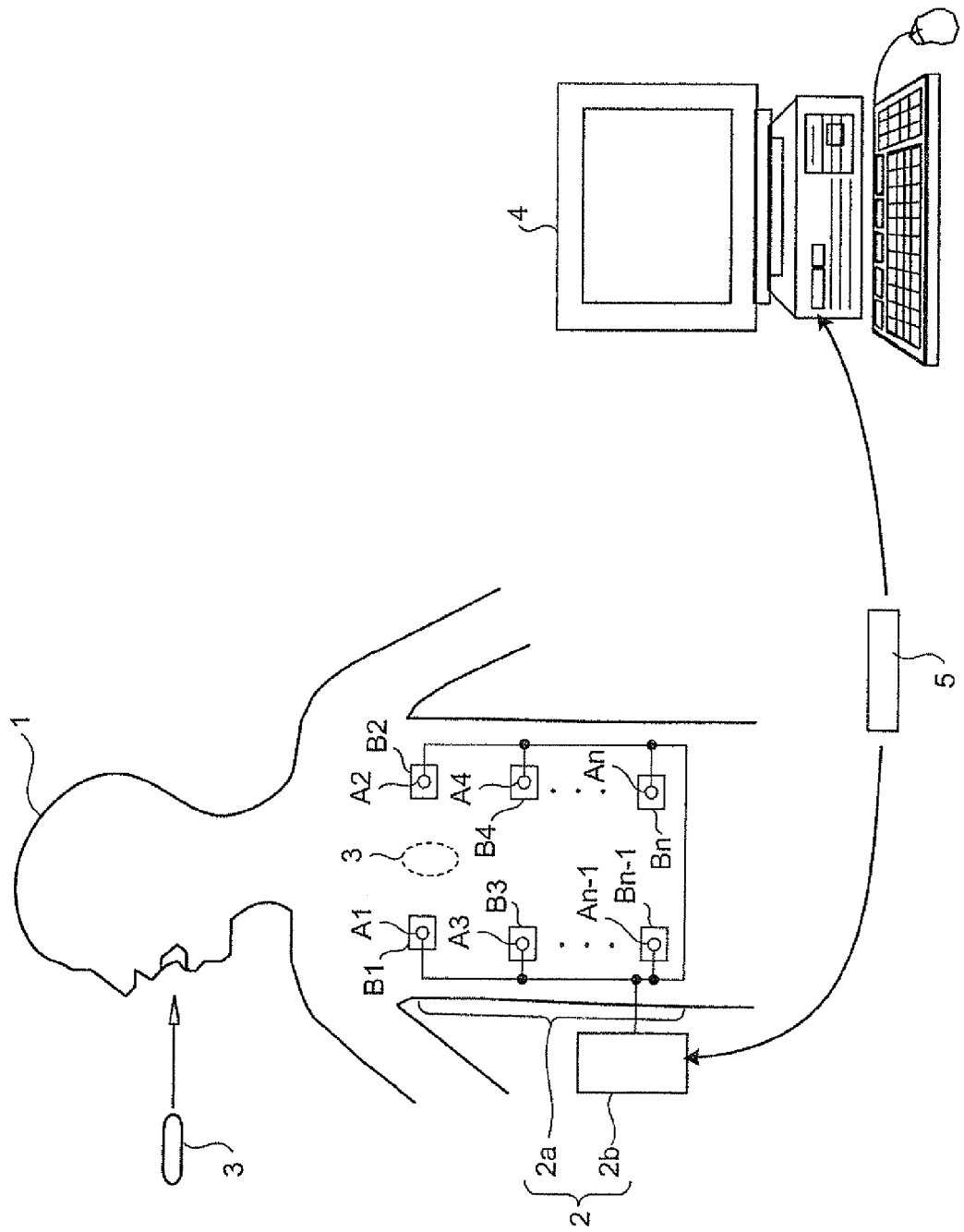
FIG. 1 is a schematic diagram of an overall structure of a wireless in-vivo information acquiring system which includes a receiving device according to a first embodiment.

1 Subject
2 Receiving device
2a Antenna group
2b External device
3 Capsule endoscope
4 Display device
5 Portable recording medium
11 Receiving circuit
12 Signal processing circuit
13 Storage unit
14 Display unit
15 Sample-and-hold circuit
16 A/D converter
17 Power supply unit
A1 to An Receiving antenna
A11 Loop portion
A12 Cable portion
A13 Resin plate
B1 to Bn Antenna cover
B11, B12 Cover member
B13 Adhesive
B14 Housing portion
B15, B19 Adhesive portion
B16 Slot
B17 Tab
B18 Fold line
B20 Non-adhesive portion
B20, B21 Hole
B22 to B25 Perforated line
B26 Strip-like member
C Control unit
C1 Selection controller
CON Connecting unit
CON1 to CONn Connector
SC Switching controller
SW Changeover switch

BEST MODE(S) FOR CARRYING OUT THE INVENTION

Exemplary embodiments of an antenna cover and an antenna apparatus according to the present invention will be described in detail below with reference to FIGS. 1 to 11. It should be noted that the present invention is not limited to the embodiments described below and various modification can be made to the embodiments without departing from the scope of the present invention. In the following description, an antenna apparatus that receives image signals obtained by a capsule endoscope (body-insertable device) will be described by way of an example.

First Embodiment

FIG. 1 is a schematic diagram of an overall structure of a wireless in-vivo information acquiring system which includes a receiving device according to a first embodiment. In FIG. 1, the wireless in-vivo information acquiring system includes a receiving device 2 that has a radio reception function, and a capsule endoscope 3 that is inserted into a subject 1 to capture images inside body cavities and that transmits data such as image signals to the receiving device 2. The wireless in-vivo information acquiring system further includes a display device 4 that displays images inside the body cavities based on the image signals received by the receiving device 2, and a portable recording medium 5 that serves to transfer data between the receiving device 2 and the display device 4. The receiving device 2 includes an antenna group 2a and an external device 2b that performs, for example, processing of received radio signals. Both the antenna group 2a and the external device 2b are carried by the subject 1.

The display device 4 serves to display images captured by the capsule endoscope 3 inside the body cavities, for example. The display device 4 has a configuration like a workstation that displays images based on data retrieved from the portable recording medium 5, for example. Specifically, the display device 4 may directly display images on a CRT display, a liquid crystal display, and the like. Alternatively the display device 4 may output images to other media as in a printer.

The portable recording medium 5 is attachable and detachable from the external device 2b and the display device 4. When the portable recording medium 5 is attached to one of the external device 2b and the display device 4, information can be output from and recorded into the portable recording medium 5. In the first embodiment, while the capsule endoscope 3 travels through the body cavities of the subject 1, the portable recording medium 5 is attached to the external device 2b and records data transmitted from the capsule endoscope 3. After the capsule endoscope 3 is discharged from the subject 1, i.e., after the imaging inside the subject 1 is finished, the portable recording medium 5 is removed from the external device 2b and attached to the display device 4. The display device 4 reads out the data recorded in the portable recording medium 5. For example, when the data transfer between the external device 2b and the display device 4 is carried out with the portable recording medium 5 which includes a CompactFlash® memory or the like, the subject 1 can move more freely during the imaging inside the body cavities compared with a time when the external device 2b and the display device 4 are directly connected by a cable. In the embodiment, the portable recording medium 5 is employed for the data transfer between the external device 2b and the display device 4. A manner of data transfer, however, is not limited to the use of the portable recording medium 5. For example, the external device 2b may have another embedded recording device, such as a hard disk, and the display device 4 and the external device 2b may be connected by a cable or by radio for data transfer.

Figure 2:
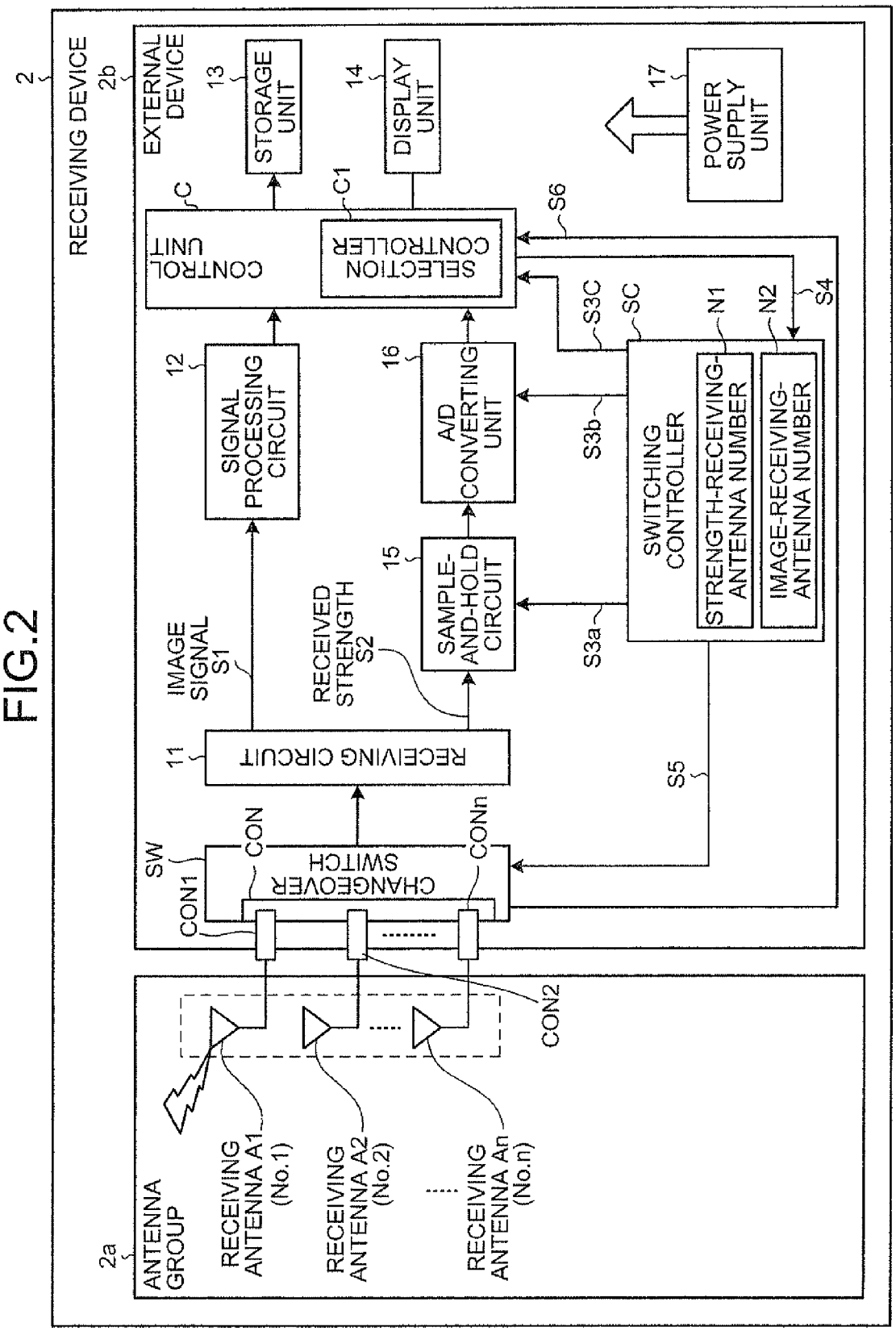
FIG. 2 is a block diagram illustrating a structure of the receiving device shown in FIG. 1.

A structure of the receiving device will be described with reference to a block diagram of FIG. 2. The receiving device 2 has a function of receiving image data obtained inside the body cavities and transmitted by radio by the capsule endoscope 3. As shown in FIG. 2, the receiving device 2 includes the antenna group 2a and the external device 2b. The antenna group 2a works as an antenna apparatus and includes receiving antennas A1 to An and antenna covers B1 to Bn (see FIG. 1) that house the receiving antennas A1 to An, respectively, and that are directly pasted onto an outer surface of the subject (human body) 1. The external device 2b performs, for example, processing of radio signals received via the antenna group 2a. The receiving antennas A1 to An may be pasted onto a surface of a garment such as a jacket the subject 1 wears.

On an outer surface of the external device 2b, a battery pack (not shown) is attached. The battery pack houses a battery for power supply. When the battery pack is attached to the external device 2b, the battery and internal elements of the external device 2b are electrically connected with each other, and the power can be supplied to the internal elements. The internal elements of the external device 2b will be described later. Further, on an upper outer surface of the external device 2b, a connecting unit CON that serves to connect the receiving antennas A1 to An to the external device 2b is provided.

Figure 3:
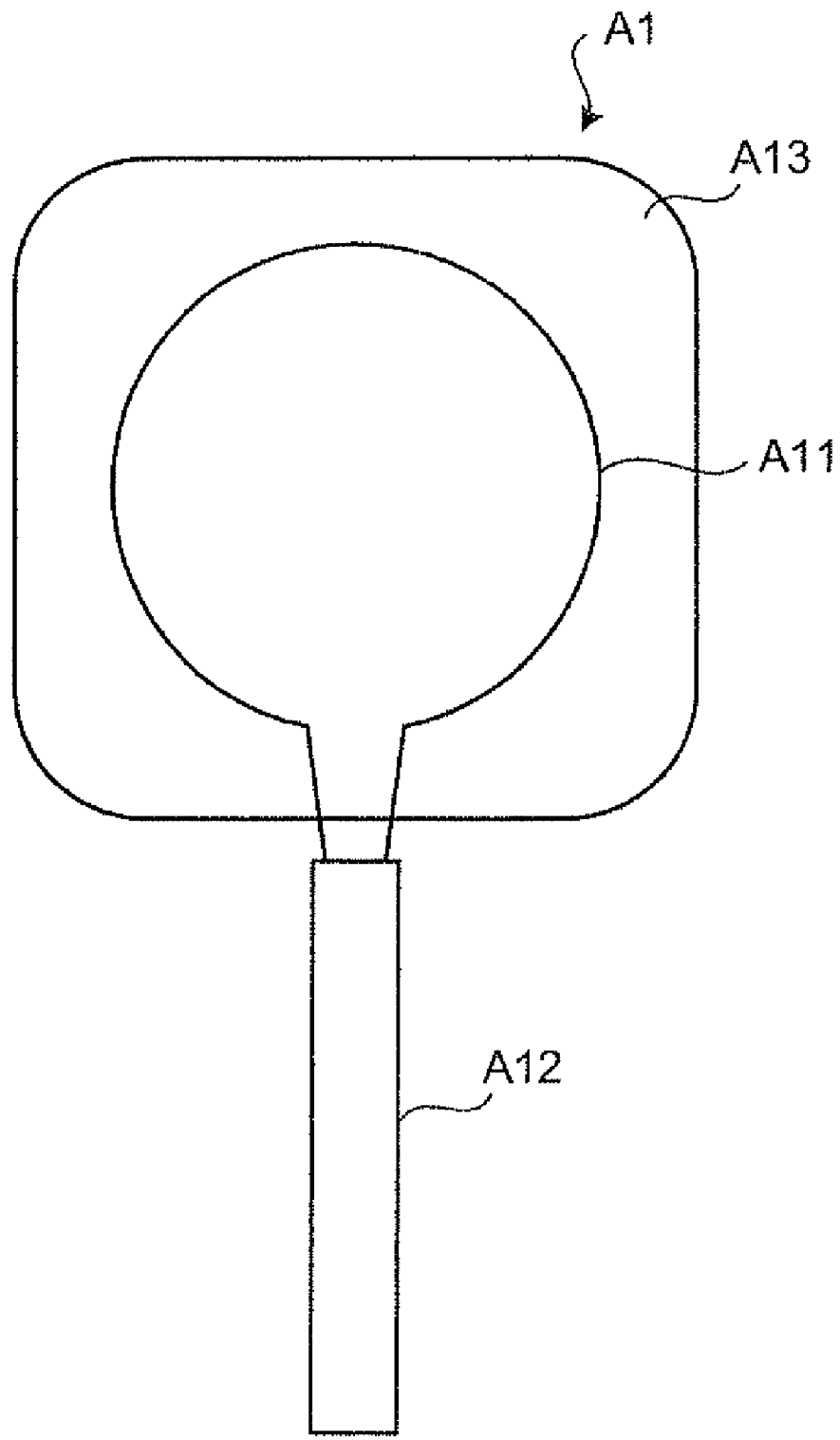
FIG. 3 is a schematic diagram of one exemplary structure of a receiving antenna shown in FIG. 2.

The receiving antennas A1 to An that serve as antenna elements have connectors CON1 to CONn, respectively. The connectors CON1 to CONn are connected to the connecting unit CON. The receiving antennas A1 to An have the same configuration. A structure of the receiving antenna A1 is shown in FIG. 3 as a representative example. In FIG. 3, the receiving antenna A1 includes a loop portion A11, a cable portion A12, and a resin plate A13. The loop portion A11 is a loop antenna, for example, and formed in a loop-like shape having one end. The cable portion A12 has one end attached to the end of the loop portion A11 and another end attached to the connector CON1. At least a portion of the loop portion A11 is buried in the resin plate A13. In the first embodiment, the loop portion A11 is entirely buried in the resin plate A13.

The resin plate A13 is a resin member as a first transparent member, and is a substantially square transparent chamfered member, for example. The resin plate A13 holds the buried loop portion A11 so as to prevent deformation and breakage thereof. Further, identification information is written on the resin plate A13, for example, at a central portion of the plate A13. The identification information indicates, for example, a position (not shown) on an outer surface of the subject 1 where the resin plate A13 is to be placed. At the time of examination, the receiving antennas A1 to An are housed inside the antenna covers B1 to Bn, respectively, and pasted onto respective predetermined positions on the outer surface of the subject 1 for use. The identification information is written on the antenna element so that the length of the cable portion A12 is set to an appropriate length suitable for the position where the antenna element is attached, and so that the correspondence between the antenna element and an examined region can be previously set. Such setting serves to prevent entanglement and breakage of the cable portion A12. According to the present invention, the receiving antennas A1 to An and the antenna covers B1 to Bn constitute antenna apparatuses, respectively. A collection of antenna apparatuses is referred to as the antenna group 2a. Further, the resin plate may be transparent only in a portion where the identification information is shown, and other portions may be semi-transparent. The identification information may be written on any position of the resin plate A13, and the position where the identification information is written is not limited to a central portion of the plate.

The external device 2b has a function of performing processing of the radio signals sent from the capsule endoscope 3. Specifically, the external device 2b includes, as shown in FIG. 2, a changeover switch SW that switches connections to the receiving antennas A1 to An, and a receiving circuit 11 that is connected as a subsequent stage to the changeover switch SW. The receiving circuit 11 amplifies and demodulates radio signals sent from the receiving antenna A1 to An to which the receiving circuit 11 is connected by switching of the changeover switch SW. Further, a signal processing circuit 12 and a sample-and-hold circuit 15 are connected to the receiving circuit 11 as subsequent stages. Still further, an A/D converter 16 is connected as a subsequent stage to the sample-and-hold circuit 15.

A control unit C has a selection controller C1 which serves as a controller. The control unit C connects the signal processing circuit 12, the A/C converter 16, a storage unit 13 which corresponds to the portable recording medium 5, the display unit 14, and a switching controller SC. The switching controller SC holds an strength-receiving-antenna number N1 and a image-receiving-antenna number N2. The switching controller SC gives a switching command to the changeover switch SW based on the number information. At the same time, the switching controller SC gives commands to the sample-and-hold circuit 15, the A/D converter 16, and the selection controller C1 to determine timing of processing. A power supply unit 17 includes the battery in the battery pack, and supplies power to each of the above described internal elements.

The changeover switch SW of the external device 2b supplies radio signals sent from the receiving antennas A1 to An to the receiving circuit 11 according to the switching command from the switching controller SC. The changeover switch SW has the connecting unit CON which serves as an antenna switching unit connecting each of the receiving antennas A1 to An to the changeover switch SW and which is provided corresponding to a position of each of the receiving antennas A1 to An.

The connecting unit CON has a disconnected antenna detecting portion (not shown) for detecting a disconnected state of each of the connectors CON1 to CONn. The disconnected antenna detecting portion is provided for each of the connectors CON1 to CONn, and the selection controller C1 can determine whether the receiving antennas A1 to An are connected to the external device 2b or not, in other words, the selection controller C1 can know a connection state of each of the connectors CON1 to CONn by detecting presence/absence of a disconnection detecting signal supplied from the disconnected antenna detecting portion.

The receiving circuit 11, as described above, amplifies and demodulates the radio signals to obtain image signals S1.

Then, the receiving circuit 11 supplies the image signals S1 to the signal processing circuit 12. At the same timer the receiving circuit 11 supplies received strength signals S2 to the sample-and-hold circuit 15. The received strength signal S2 indicates intensity of an electric field of the amplified received radio signal. The signal processing circuit 12 performs processing to obtain image data. The image data is stored in the storage unit 13 under the control of the control unit C and also output to the display unit 14 for display. The sample-and-hold circuit 15 samples and holds the received strength signal S2, and supplies the resulting signal to the A/D converter 16 which converts the supplied signal to a digital signal. The resulting digital signal is taken in by the control unit C. The control unit C selects a receiving antenna which has received a signal with a highest electric field intensity as a receiving antenna for a image signal period. At the same time, the control unit C sequentially selects receiving antennas other than the one selected for the image signal period as a receiving antenna for an intensity receiving period. The control unit C outputs a number of each selected receiving antenna as either the image-receiving-antenna number N2 or the strength-receiving-antenna number N1 as a signal S4 to the switching controller SC. Here, the selection controller C1 sets only the receiving antennas A1 to An that are actually connected as the receiving antennas to which the switching can be performed based on a signal S6. Further, the control unit C stores an intensity of a received electric field during the intensity receiving period and an intensity of a received electric field during the video receiving period in the storage unit 13 together with the image data in association with the receiving antenna selected at the time. The intensity of the received electric field at each receiving antenna is stored and utilized as information to calculate where the capsule endoscope 3 resides in the body cavity when the image data is received.

The switching controller SC stores the strength-receiving-antenna number N1 and the image-receiving-antenna number N2 as instructed by the selection controller C1. The switching controller SC supplies a signal S5 to the changeover switch SW so as to give a command to the changeover switch SW to selectively connect a receiving antenna corresponding to the strength-receiving-antenna number N1 among the receiving antennas A1 to An during the intensity receiving period, and to give a command to the changeover switch SW to selectively connect a receiving antenna corresponding to the image-receiving-antenna number N2 among the receiving antennas A1 to An during the video receiving period. At the same timer the switching controller SC supplies a signal S3$a$ to the sample-and-hold circuit 15 so as to give a command on sample-and-hold timing, a signal S3$b$ to the A/D converter 16 so as to give a command on A/D converting timing, and a signal S3$c$ to the selection controller C1 so as to give a command on selective controlling timing.

Figure 4:
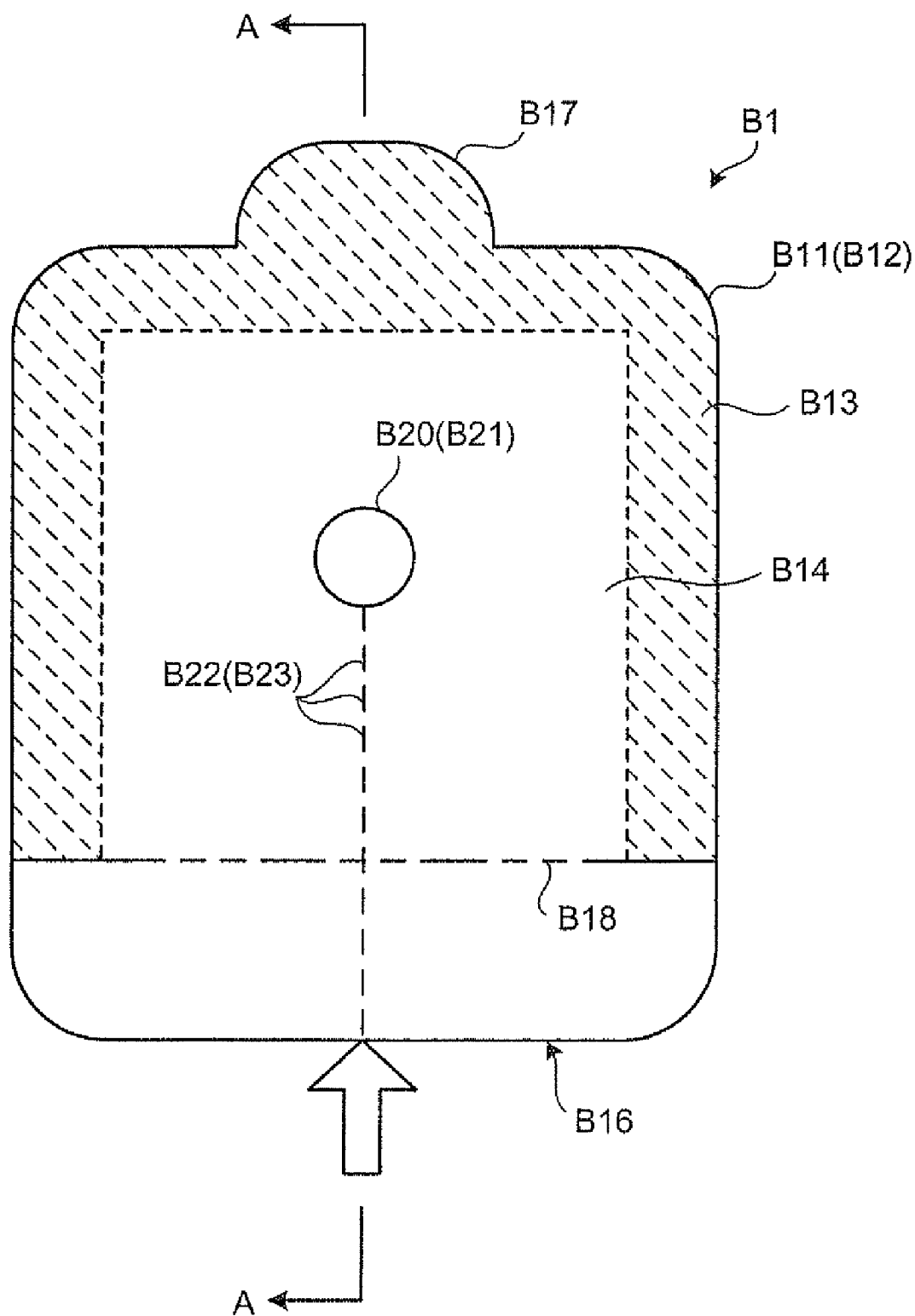
FIG. 4 is a schematic diagram of a structure of an antenna cover according to the first embodiment.
Figure 5:
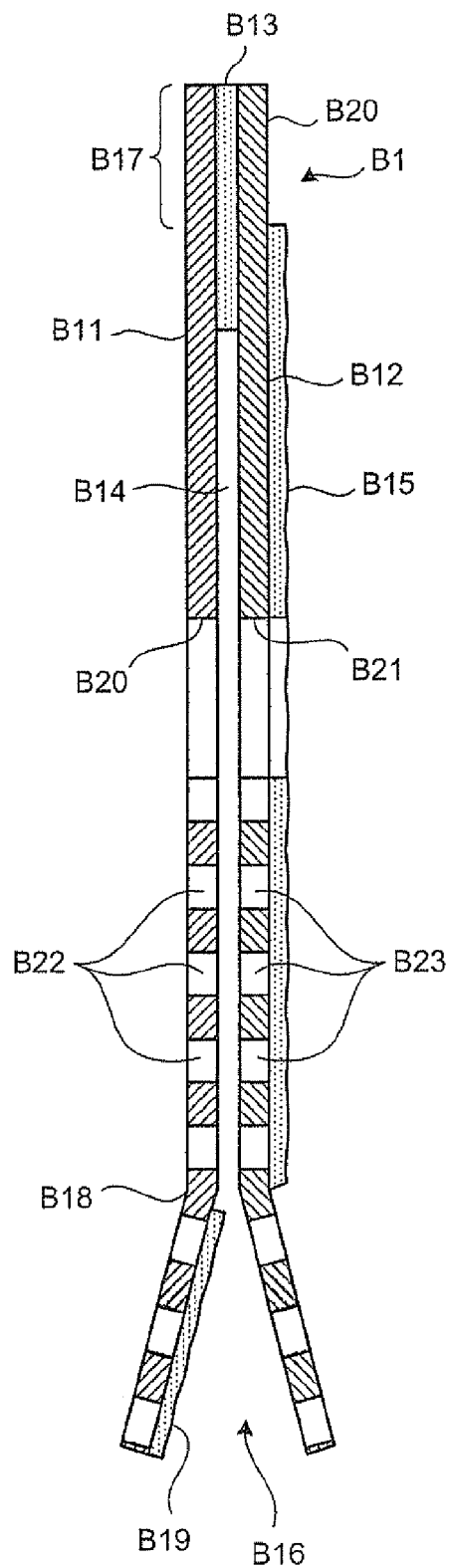
FIG. 5 is a sectional view of the antenna cover along line A-A of FIG. 4.

A structure of the antenna cover will be described. The antenna covers B1 to Bn have the same structure. Here, the structure of the antenna cover B1 is shown in FIGS. 4 and 5 as a representative example. FIG. 4 is a schematic diagram illustrating the structure of the antenna cover according to the first embodiment. FIG. 5 is a sectional view of the antenna cover along line A-A of FIG. 4. In FIGS. 4 and 5, the antenna cover B1 includes two cover members B11 and B12. Each of the cover members B11 and B12 is formed of a substantially rectangular chamfered paper, non-woven fabric, cellophane, or the like. Adhesive B13 is applied on an edge region shown by a pattern of slanted chain lines in FIG. 4, and the cover members B11 and B12 adhere with each other in the edge region due to the adhesive B13. The edge region, where the cover members B11 and B12 adhere with each other by adhesive B13, is provided in edge portion along three sides of each of the cover members B11 and B12. When the cover members B11 and B12 adhere with each other, a housing portion B14 is formed in a central region between opposing faces of the cover members B11 and B12. The housing portion B14 serves to house the antenna element. An inner shape of the housing portion B14 is substantially the same as an outer shape of the antenna element (resin plate A13). Further, as shown in FIG. 5, an adhesive portion B15 is formed on an outer surface of the cover member B12 and extends over a portion other than a tab B17 which will be described later. Acrylic adhesive is applied on the adhesive portion B15, for example, and allows the antenna cover B to be pasted and fixed on to an outer surface of the subject 1. Before the antenna cover B1 is used, the adhesive portion B15 and (cover member B12 side of) the tab B17 are covered by a release paper (not shown) so that the adhesion is not allowed. When the antenna cover B is to be used, the release paper is peeled off to expose the adhesive portion B15 so that the antenna cover B1 can adhere.

In addition, the antenna cover B has a slot B16 through which the antenna element can be inserted into the housing portion B14. The slot B16 is provided in another edge region to which adhesive is not applied and which extends along one side of the antenna cover B1. The antenna cover B further has a tab B17 which is a protruding portion extending from one side of the attached edge region. On a housing portion B14 side of the slot B16, a fold line B18 is formed as shown by two-dot chain line in FIG. 4 in order to facilitate the insertion of the antenna element. Further, an adhesive portion B19 is provided on an inner surface of the cover member B11 which forms the slot B16. On the adhesive portion B19, acrylic adhesive is applied, for example. If the inner surface of the cover member B11 is pasted onto the opposing inner surface of the cover member B12 at the slot B16, while the antenna element is placed inside the housing portion B14, the slot B16 can be closed and the antenna member can be secured. It is sufficient if the fold line B18 and the adhesive portion B19 are formed in at least one of the cover members B11 and B12. Before the use of the antenna cover B, a release paper (not shown) is placed onto the adhesive portion B19 so as to prevent adhesion. When the antenna cover B1 is used, the release paper is peeled off to expose the adhesive portion B19, so as to allow adhesion.

The tab B17 protrudes from one side of the pasted edge region. For example, in the first embodiment, the tab B17 protrudes from the opposite side to the side of the slot B16. At the same time, a non-adhesive portion B20 is formed on an outer surface of the cover member B12 in a portion forming the tab B17. On the non-adhesive portion B20, no adhesive is applied. In brief, the tab B17 is formed so that an operator can hold the tab B17 on removing the antenna cover B1 from the outer surface of the subject 1 after the examination. In addition, since no adhesive is applied on the tab B17, the release paper covering the outer surface of the cover member B12 can be easily removed at the time of use of the antenna cover B1. In the first embodiment, the tab B17 protrudes from the side opposite to the slot B16. The present invention, however, is not limited to such an arrangement. The tab B17 may be formed on both the opposite side of the slot B16 and at least one of the right and the left side of each of the cover members B11 and B12.

Figure 6:
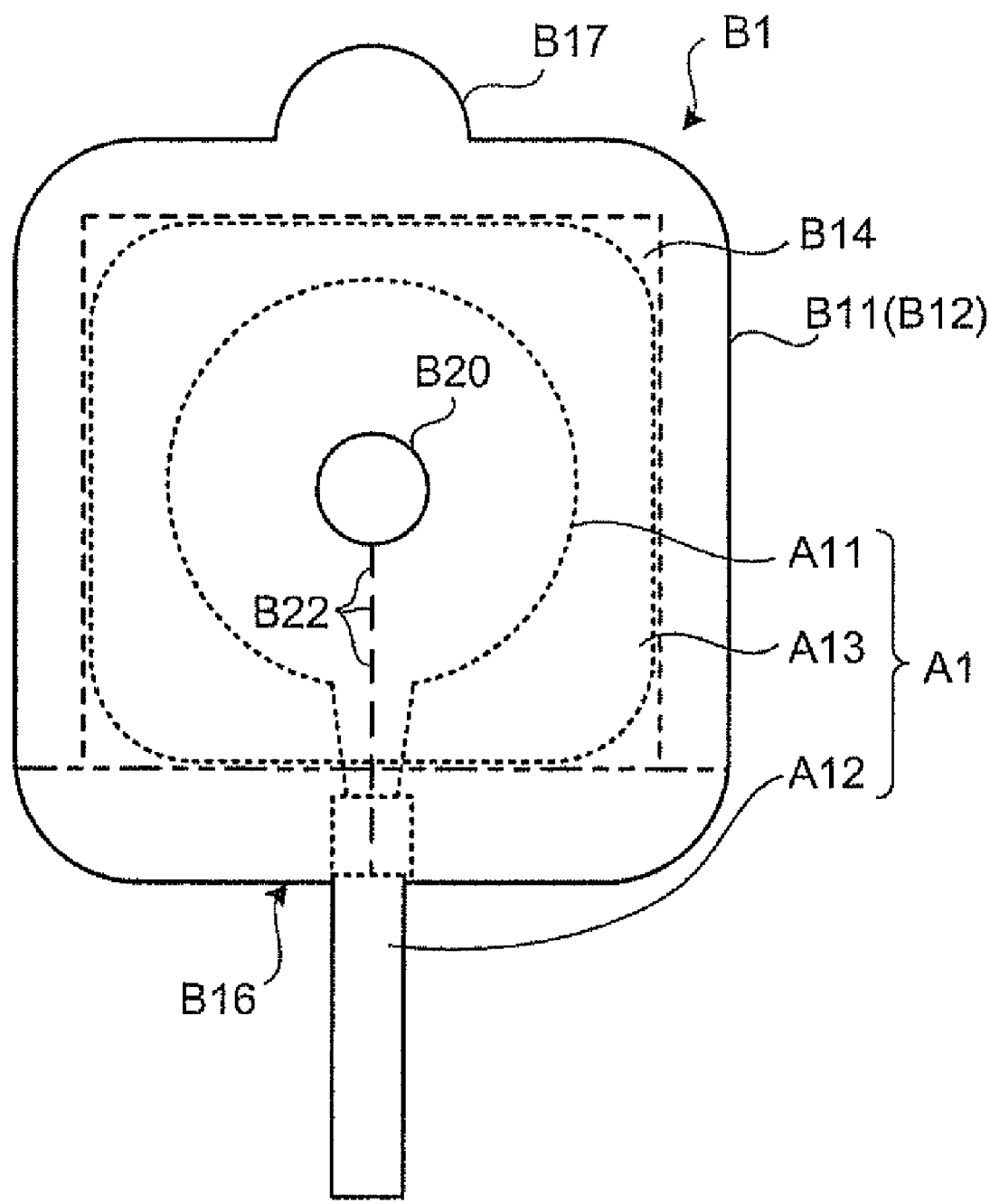
FIG. 6 shows the antenna cover of FIG. 4 in which the receiving antenna of FIG. 3 is inserted.

The antenna cover B1 further has circular holes B20 and B21 that are formed substantially at the center of the housing portion B14 and penetrate the respective cover members B11 and B12 that are combined to form the housing portion B14 therebetween like a bag. The circular holes B20 and B21 serve as openings (windows). Inner diameters of the holes 520 and B21 are substantially the same with each other, and smaller than the inner diameter of the loop portion A11 of the antenna element. When the antenna cover B1 covering the antenna element is pasted onto the outer surface of the subject 1, the positions of the holes B20 and B21 are aligned with the position of a marker provided on the outer surface of the subject 1 in advance. Thus, it is possible to arrange the loop antenna at a position where the loop antenna can easily receive the radio signals from the capsule endoscope 3 while the capsule endoscope 3 performs examination on a predetermined region. In addition, since the internal shape of the housing portion B14 of the antenna cover B1 is substantially the same as the external shape of the antenna element, the antenna element, such as the receiving antenna A1, is properly positioned inside the antenna cover B1 when inserted into the housing portion B14 as shown in FIG. 6. Thereafter, the operator can check the marker on the outer surface of the subject 1 through the holes B20 and B21 from the cover member B11 side, and align the holes B20 and B21 with the marker. Thus, the antenna element, i.e., the loop antenna can be properly positioned. The openings of the holes B20 and B21 can be set to any positions depending on the position of the identification information of the antenna element, and the position is not limited to the center.

Figure 7:
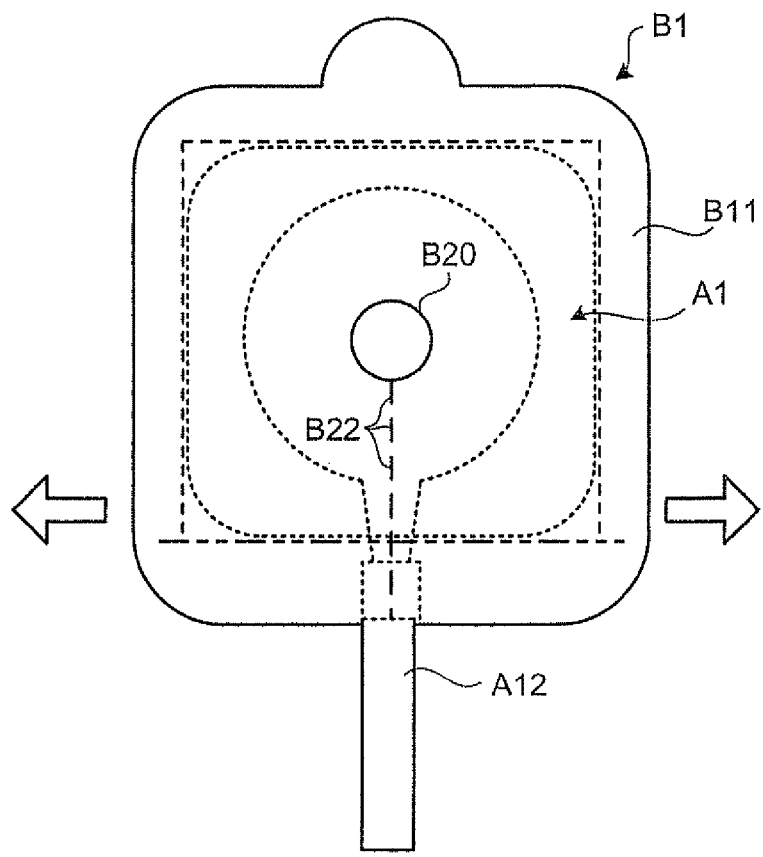
FIG. 7 illustrates how to remove the receiving antenna from the antenna cover in a state as shown in FIG. 6.

The antenna cover B1 further has perforations (perforated lines) B22 and B23 in the cover members B11 and B12, respectively. The perforations B22 and B23 serve as breakable linear portions and run from the slot B16 towards the holes B20 and B21, respectively, in other words, in an opposite direction from the direction of extension of the cable portion A12 of the antenna element. The perforated lines B22 and B23 are formed before the release paper is placed over the adhesive portion B15. As shown in FIG. 7, when an operator pulls a right side portion and a left side portion of the antenna cover B1 in respective directions of arrows after the examination, the cover members B11 and B12 are broken along the perforated lines, whereby the operator can easily remove the receiving antenna A1. In addition, since the cover members B11 and B12 are broken in the same direction as the direction of extension of the cable portion A12, the cable portion A12 is not subjected to an excessive force, whereby failure, such as disconnection, can be prevented. Since the antenna cover B1 is broken along the perforated line, it is preferable to form the antenna cover B1 with a replaceable material, such as paper, non-woven fabric, and cellophane, for the antenna element. However, any material can be employed as far as it is breakable. The perforated lines B22 and B23 may be formed so as to run from the slot B16 through the holes B20 and B21 to the tab B17.

An operation from pasting of the antenna element on the subject to removing of the antenna element after the examination will be described. First, the operator inserts the receiving antenna A1 shown in FIG. 3 inside the antenna cover B1 shown in FIG. 4 before the examination (see FIG. 6). Then, the operator peels off the release paper (not shown) covering the adhesive portion B19 of the slot B16 to paste the cover members B11 and B12 with each other at the slot B16, thereby closing the slot B16 and securing the antenna element. Thus, the receiving antenna A1 is properly positioned inside the antenna cover B1, and the operator can recognize the identification information on the resin plate A13 of the receiving antenna A1 through the holes B20 and B21. Then, the operator peels off the release paper (not shown) covering the adhesive portion B15 of the cover member B12. Further, the operator aligns the holes B20 and B21 with the marker while checking the marker on the outer surface of the subject 1 through the holes B20 and B21 from the cover member B11 side. Then, while maintaining the alignment, the operator pastes the antenna cover B1 at a predetermined position on the outer surface of the subject 1, and starts examination.

After finishing the examination, the operator holds the tab B17 and removes the antenna cover B1 from the outer surface of the subject 1. Then, as shown in FIG. 7, the operator pulls the right and the left side portions of the antenna cover B1 in the directions of arrows thereby breaking the cover members B11 and B12 along the perforated lines. Thus, the slot B16 side of the antenna cover B1 is made open, and the operator can readily remove the receiving antenna A1 from the antenna cover B1.

As can be seen from the foregoing, in the first embodiment, the receiving antenna is inserted into and secured inside the antenna cover, and the antenna cover thus housing the receiving antenna is pasted at a predetermined position on the outer surface of the subject. Therefore, the operation to attach the receiving antenna to the antenna cover or to the subject before the examination and the operation to remove the receiving antenna from the antenna cover or from the subject after the examination can be readily performed. Since the operations become less cumbersome, the time required for the operation is shortened, and accordingly, the time required for the examination can be shortened.

Further, in the first embodiment, the antenna cover made of a replaceable material such as paper, non-woven fabric, or cellophane is provided for the receiving antenna. Therefore, the operation to attach the receiving antenna to the antenna cover or to the subject before the examination and the operation to remove the receiving antenna from the antenna cover or from the subject after the examination can be more readily performed.

In the first embodiment, the antenna cover houses the receiving antenna by placing the receiving antenna inserted from the slot in the housing portion formed between the cover members. In addition, the adhesive portion is provided on a predetermined surface of the cover member so that the cover member adheres to the subject. Therefore, the operation to attach the receiving antenna to the antenna cover or to the subject before the examination and the operation to remove the receiving antenna from the antenna cover or from the subject after the examination can be more readily performed.

Further, in the first embodiment, the tab which has the non-adhesive portion on a predetermined surface protrudes from the edge of the cover member. Therefore, the operation to attach the receiving antenna to the antenna cover or to the subject before the examination and the operation to remove the receiving antenna from the antenna cover or from the subject after the examination can be readily performed. At the same time, the release paper covering the adhesive portion and the non-adhesive portion can be easily removed.

Still further, in the first embodiment, the hole is provided on each of the opposing surfaces of the cover members that form the housing portion. Therefore, the operator can recognize the outer surface of the subject via the antenna cover. In addition, the receiving antenna can be easily removed from the outer surface of the subject.

Still further, in the first embodiment, the continuous perforated line is formed on the cover member so that, when the receiving antenna is to be removed from the antenna cover, the cover member can be broken along the perforated line acted upon by an external force. In the first embodiment, the external force is applied in a direction perpendicular to the direction of extension of the cable in order to remove the receiving antenna. Therefore, the operation of removal applies less force on the cable, and failure such as disconnection is not caused during the removal operation.

Second Embodiment

Figure 8:
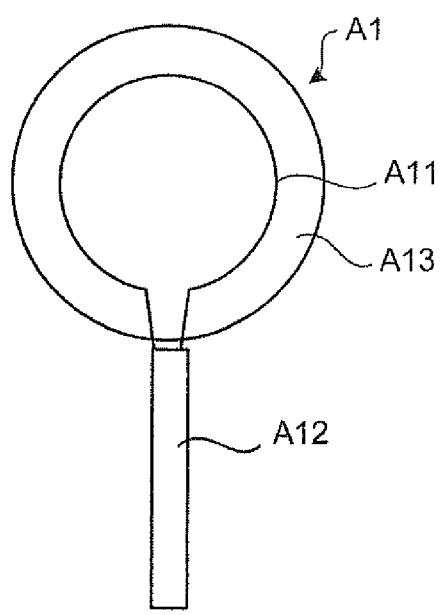
FIG. 8 is a schematic diagram illustrating another exemplary structure of the receiving antenna shown in FIG. 2.
Figure 9:
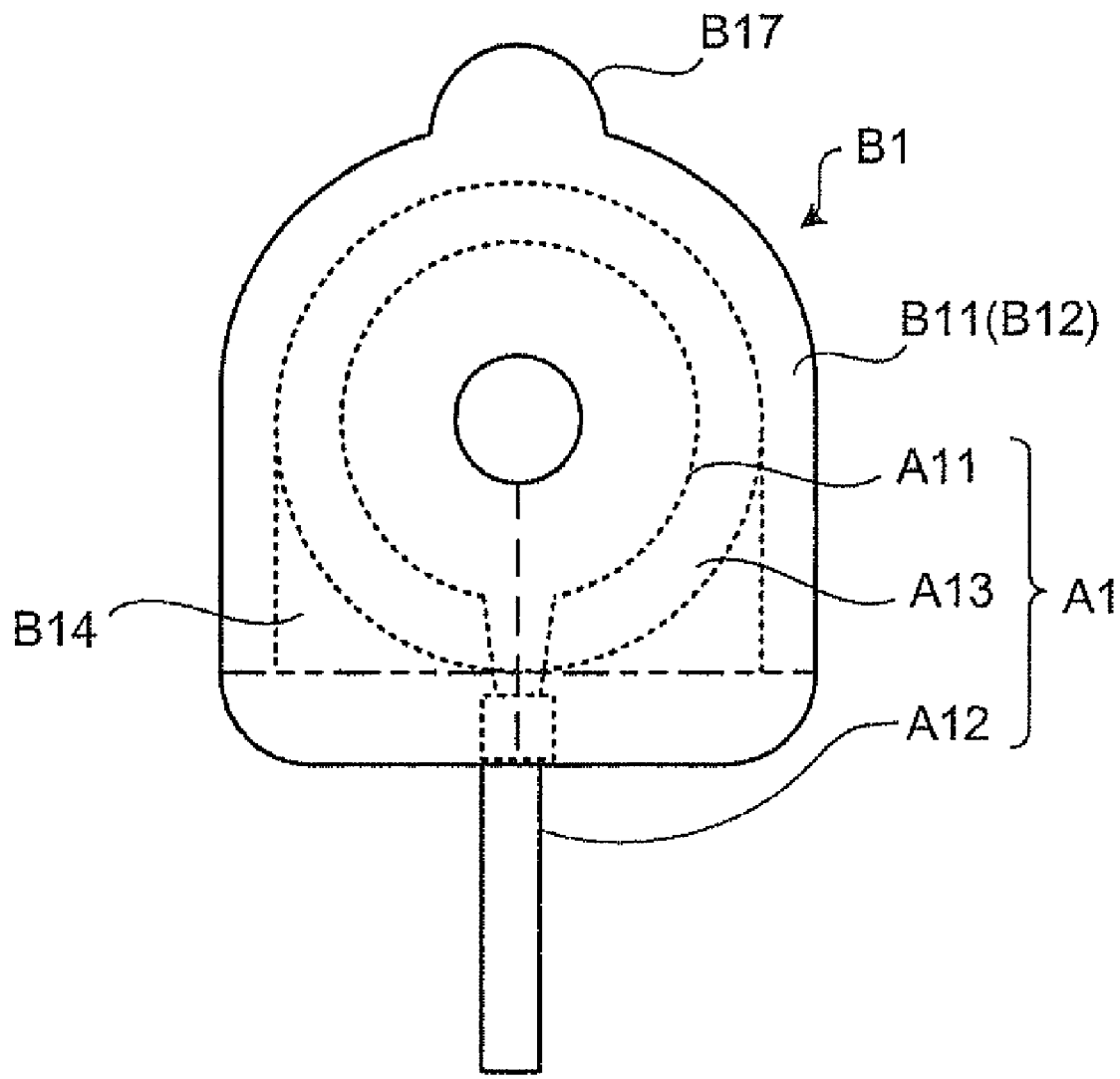
FIG. 9 is a schematic diagram illustrating a structure of an antenna cover according to a second embodiment.

FIG. 8 is a schematic diagram of another exemplary structure of the receiving antenna shown in FIG. 2. FIG. 9 is a schematic diagram showing a structure of the antenna cover according to a second embodiment. In the drawings referred to below, elements similar to the elements of the receiving antenna and the antenna cover shown in FIGS. 3 and 4 will be indicated by the same reference character for convenience of description.

In the above description of the first embodiment, the receiving antenna A1 that includes a substantially rectangular resin plate A13, and the substantially rectangular antenna cover B1 that houses the receiving antenna A1 are described. The present invention, however, is not limited to the first embodiment. Modifications as shown in FIGS. 8 and 9 can be employed, for example. In the second embodiment, the antenna apparatus includes the receiving antenna A1 which has a substantially circular resin plate A13, and the semi-circular, semi-rectangular antenna cover B which is formed in a semi-circular shape on the side on which the tab B17 is provided in the cover members B11 and B12 as shown in FIG. 9. The housing portion B14 is semi-circular and semi-rectangular as well, in accordance with the exterior shape of the antenna cover B1.

The second embodiment has the same advantages as those of the first embodiment. In addition, since one side of the antenna cover is semi-circular, an area of the adhesive portion is smaller than that in the rectangular antenna cover of the first embodiment. Therefore, when the operator holds the tab and removes the antenna cover from the outer surface of the subject, the adhesion creates less resistance against the removal, whereby the antenna cover can be more easily removed.

Third Embodiment

Figure 10:
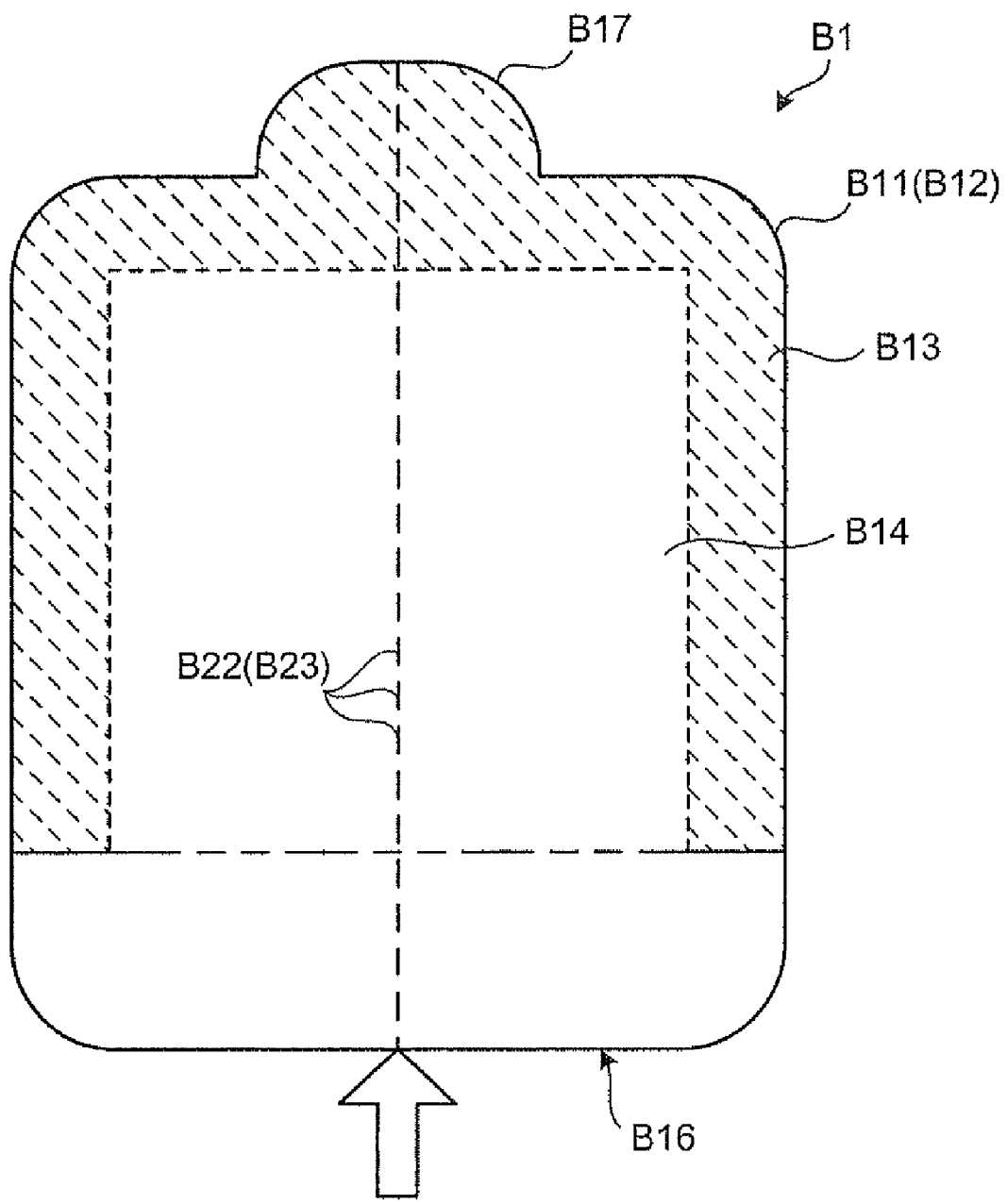
FIG. 10 is a schematic diagram illustrating one exemplary structure of an antenna cover according to a third embodiment.

FIG. 10 is a schematic diagram of an exemplary structure of the antenna cover according to a third embodiment. In the third embodiment, it is assumed that a material such as cellophane is employed in the cover members B11 and B12 as a second transparent member. Since the cover members B11 and B12 are formed of transparent cellophane in FIG. 10, the holes B20 and B21 at the central portion of the housing portion B14 are not necessary. Further, the perforated lines B22 and B23 run from the slot B16 to the tab B17 in the cover members B11 and B12, respectively.

The third embodiment has the similar advantages as those of the first embodiment. In addition, since the hole in the cover member is not required, a manufacturing process is simplified and manufacturing time is reduced. Further, manufacturing cost may be reduced.

FIG. 11 is a schematic diagram of another exemplary structure of the antenna cover according to the third embodiment. In the example, plural perforated lines are formed in each of the cover members B11 and B12. For example, two perforated lines B22 and B24, and two perforated lines B23 and B25 are formed with a predetermined distance therebetween on the cover members B11 and B12, respectively. To remove the receiving antenna, the operator holds a strip-like member B26 formed between the perforated lines B22 and B24 at the slot B16 side, for example, and pulls the strip-like member B26 in a direction of arrow in FIG. 11. Then, the strip-like member B26 is separated from other portions along the perforated lines B22 and B24, allowing the removal of the receiving antenna.

The above described example has the same advantages as those in the first example of the third embodiment mentioned above. In addition, since a wide portion of the cover member is removed, the receiving antenna can be removed more easily.

The antenna cover according to the present invention is not limited to the above described embodiments, and various modifications can be contemplated. For example, the cover member B11 may be formed from two sheet-like portions. Two portions overlap with each other like a double door at a position corresponding to a central line of the perforated lines mentioned above, dissimilar to the arrangement with the perforated line shown in FIG. 10. To remove the receiving antenna, the operator holds two overlapping edges and pulls one to the right and another to the left as indicated in the drawing, thereby opening the cover member B11 slidingly. Since the operator holds and pulls the cover members alone slidingly, the removal operation applies even less force on the cable, whereby the failure such as disconnection can be prevented.

Further in the present invention, a member whose strength decreases when the heat is applied may be employed in the cover members B11 and B12, for example. A deformable portion (breakable portion), which changes its nature when the heat is applied, may be provided in place of the perforated line in a region corresponding to the central line of the perforated line. Therefore, the cover member can be broken more easily when acted upon by an external force.

Still further, in the present invention, a region corresponding to the central line of the perforated line may be thinned in the cover member, so that a thin portion (breakable portion) is provided instead of the perforated lines in the cover members B11 and B12. Then, the cover member can be broken easily by an external force.

Still further, in the present invention, a strip-like member may be formed with a material different from the material of the cover members B11 and B12, and employed in place of the strip-like member B26. The cover member B11 may include two sheet-like portions. The strip-like member overlaps with and adheres to a side of each of the two sheet-like portions along a portion corresponding to the central line of the perforated line. To remove the receiving antenna, the operator holds and peels off the overlapping strip-like member. Thus, the cover member can be easily broken.

INDUSTRIAL APPLICABILITY

The antenna cover according to the present invention is useful for a medical observation apparatus, such as a capsule endoscope, which is introduced inside the human body and is employed for an observation of an examined region. In particular, the antenna cover according to the present invention is suitable for simplifying the attachment of the antenna element to the antenna cover or to the subject before the examination and for removing the antenna element from the antenna cover and from the subject after the examination.

The invention claimed is:
1. An antenna cover comprising:
a cover member which forms a housing portion inside, the housing portion being able to accommodate at least a portion of an antenna element;
a slot which is formed in the cover member, and through which the antenna element can be inserted into the housing portion;

an adhesive portion which is formed on a predetermined surface of the cover member and which has adhesiveness to allow the cover member to adhere onto a subject; and a non-adhesive portion which is formed on a same predetermined surface of the cover member as the predetermined surface on which the adhesive portion is formed, and which has non-adhesiveness.

2. The antenna cover according to claim 1, wherein the antenna cover further includes an extending portion which extends from an edge of the cover member, and the non-adhesive portion is provided on the extending portion at a side of the predetermined surface on which the adhesive portion is formed.

3. An antenna apparatus, comprising:

at least one antenna element; and an antenna cover which can house at least a portion of the antenna element, the antenna cover including a cover member which forms a housing portion inside, the housing portion being able to accommodate at least a portion of an antenna element;

a slot which is formed in the cover member, and through which the antenna element can be inserted into the housing portion;

an adhesive portion which is formed on a predetermined surface of the cover member and which has adhesiveness to paste the cover member onto a subject; and a non-adhesive portion which is formed on a same predetermined surface of the cover member as the predetermined surface on which the adhesive portion is formed, and which has non-adhesiveness.

4. The antenna apparatus according to claim 3, wherein the antenna cover further includes an extending portion which extends from an edge of the cover member, and the non-adhesive portion is provided on the extending portion at a side of the predetermined surface on which the adhesive portion is formed.

5. The antenna apparatus according to claim 3, wherein the cover member is formed with sheets of materials such as paper, non-woven fabric, and cellophane pasted with each other.

* * * * *